United States Patent
Bar-Tal

(10) Patent No.: US 10,517,612 B2
(45) Date of Patent: Dec. 31, 2019

(54) NAIL HOLE GUIDING SYSTEM

(71) Applicant: Biosense Webster (Israel) Ltd., Yokneam (IL)

(72) Inventor: Meir Bar-Tal, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 253 days.

(21) Appl. No.: 15/708,357

(22) Filed: Sep. 19, 2017

(65) Prior Publication Data

US 2019/0083115 A1    Mar. 21, 2019

(51) Int. Cl.
*A61B 17/17* (2006.01)
*A61B 34/20* (2016.01)
(Continued)

(52) U.S. Cl.
CPC ...... *A61B 17/1717* (2013.01); *A61B 17/1703* (2013.01); *A61B 17/1707* (2013.01); *A61B 17/1725* (2013.01); *A61B 34/20* (2016.02); *G05B 19/402* (2013.01); *A61B 90/37* (2016.02); *A61B 90/39* (2016.02); *A61B 90/98* (2016.02); *A61B 2017/0092* (2013.01); *A61B 2017/00221* (2013.01); *A61B 2034/2051* (2016.02); *A61B 2034/2072* (2016.02); *A61B 2090/101* (2016.02); *A61B 2090/364* (2016.02); *A61B 2090/374* (2016.02); *A61B 2090/376* (2016.02); *A61B 2090/3762* (2016.02); *A61B 2090/3764* (2016.02); *A61B 2090/397* (2016.02); *A61B 2090/3966* (2016.02); *G05B 2219/45129* (2013.01)

(58) Field of Classification Search
CPC . A61B 17/17; A61B 17/1717; A61B 17/1707; G05B 19/402
See application file for complete search history.

(56) References Cited

U.S. PATENT DOCUMENTS 6,147,480 A    11/2000   Osadchy
6,373,240 B1    4/2002   Govari
(Continued)

FOREIGN PATENT DOCUMENTS

FR       2743489 A1   7/1997
WO    WO 96/05768 A1   2/1996
(Continued)

OTHER PUBLICATIONS

European Extended Search Report for corresponding European patent application No. 18195111.2, dated Feb. 19, 2019.

*Primary Examiner* — Christopher J Beccia
(74) *Attorney, Agent, or Firm* — Notaro, Michalos & Zaccaria P.C.

(57) ABSTRACT

A jig for placing a screw to stabilize a femoral nail comprises a shell, a drill guide assembly movably mounted on the shell, and having a plurality of radiopaque markers affixed thereon, a magnetic field generator, and a plurality of magnetic location sensors responsive to magnetic fields produced by the magnetic field generator. A position processor is operative to compute positional information of the magnetic location sensors based on signals communicated thereto. The positional information is placed in registration with an anatomical image so that the drill guide assembly can be aligned with a transverse bore in the femoral nail.

18 Claims, 10 Drawing Sheets

(51) Int. Cl.
*G05B 19/402* (2006.01)
*A61B 90/00* (2016.01)
*A61B 17/00* (2006.01)
*A61B 90/10* (2016.01)
*A61B 90/98* (2016.01)

(56) References Cited

U.S. PATENT DOCUMENTS

| | | |
|---|---|---|
| 6,484,118 B1 | 11/2002 | Govari |
| 6,690,963 B2 | 2/2004 | Ben Haim |
| 6,995,729 B2 | 2/2006 | Govari |
| 7,321,228 B2 | 1/2008 | Govari |
| 7,397,364 B2 | 7/2008 | Govari |
| 7,729,742 B2 | 6/2010 | Govari |
| 7,974,680 B2 | 7/2011 | Govari |
| 8,046,050 B2 | 10/2011 | Govari |
| 8,814,868 B2 | 8/2014 | Janna |
| 2003/0120150 A1 | 6/2003 | Govari |
| 2008/0086145 A1* | 4/2008 | Sherman ............ A61B 17/1707 606/97 |
| 2010/0274256 A1 | 10/2010 | Ritchey |
| 2012/0130434 A1* | 5/2012 | Stemniski ............ A61B 17/15 606/300 |
| 2012/0232561 A1 | 9/2012 | Fernandez |
| 2012/0323247 A1 | 12/2012 | Bettenga |
| 2013/0090662 A1* | 4/2013 | Hanson ............ A61B 17/1739 606/96 |
| 2014/0114173 A1 | 4/2014 | Bar-Tal |
| 2014/0163557 A1 | 6/2014 | Beyar |
| 2015/0173643 A1 | 6/2015 | Govari |
| 2017/0007155 A1 | 1/2017 | Gliner |
| 2017/0007156 A1 | 1/2017 | Govari |
| 2017/0079553 A1 | 3/2017 | Gliner |
| 2017/0103505 A1 | 4/2017 | Demri |

FOREIGN PATENT DOCUMENTS

| | | |
|---|---|---|
| WO | 2011/029934 A1 | 3/2011 |
| WO | 2011/063279 A1 | 5/2011 |

* cited by examiner

NAIL HOLE GUIDING SYSTEM

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

This invention relates to orthopedic prostheses. More particularly, this invention relates to medical instruments for implanting a medullary nail using data processing equipment.

2. Description of the Related Art

Positioning an intramedullary nail in a long bone is a complicated process, because after positioning the nail must be locked in place. The locking is performed by attaching screws orthogonally to the nail, at the proximal and distal ends of the nail, by drilling through the bone to holes that have been preformed in the nail. Typically, this is not a problem for the proximal end, since this end is closer to the exterior of the patient, so the position of the proximal hole may be well estimated. However, the position of the distal hole is problematic, since the nail may bend when it is inserted into the bone. The position needs to be known, in order to inform the operator properly drilled holes for the screws, both as to alignment and depth.

Prior art methods, such as the disclosure of U.S. Patent Application Publication No. 2010/0274256 requires placement of a landmark or beacon on the nail so as to be able to locate the distal hole. However this complicates matters.

SUMMARY OF THE INVENTION

According to disclosed embodiments of the invention, a jig is used to insert the nail. The jig comprises a plate that has electromagnetic sensors and X-ray fiducial elements attached to the plate. Positions of the electromagnetic sensors are known to a position processing system that includes magnetic field generators. The jig also has a drill guide. The X-ray fiducial elements enable the position of the distal end nail hole to be located with reference to the drill guide of the jig when two orthogonal X-ray images are taken. The position information derived from readings of the electromagnetic sensors on the jig enable the jig to be registered with the position processing system.

The jig is moved under fluoroscopy such that the drill guide aligns with the distal end hole. Since the jig is in registration with the fluoroscopic images of the nail, the position of the distal nail hole is also known in coordinates of the magnetic generator system. The fluoroscope may then be switched off. A drill having an attached electromagnetic sensor can be then advanced to the appropriate depth while being monitored by the position processing system. The information read from the sensor on the drill by the position processing system allows the depth to which the drill bit of the drill penetrates to be measured.

There is provided according to embodiments of the invention a shell, conformable to a limb of a patient, a drill guide assembly movably mounted on the shell and having a plurality of radiopaque markers affixed thereon, a magnetic field generator, and a plurality of magnetic location sensors responsive to magnetic fields produced by the magnetic field generator. A position processor is operative to compute positional information of the magnetic location sensors based on signals communicated thereto. Using the radiopaque markers, the positional information is registered with an anatomical image.

According to an additional aspect of the apparatus, the position processor is disposed on the shell.

According to another aspect of the apparatus, the position processor also includes circuitry for driving the magnetic field generator.

According to one aspect of the apparatus, the shell and the drill guide assembly are radiolucent.

According to a further aspect of the apparatus, there are three magnetic location sensors.

According to yet another aspect of the apparatus, there are five magnetic location sensors.

According to yet another aspect of the apparatus, the drill guide assembly includes a ball joint having a bore formed therethrough and dimensioned to admit a drill bit.

According to one aspect of the apparatus, one of the magnetic location sensors is disposed on the ball joint.

Still another aspect of the apparatus includes a first flange and a second flange attached to the shell, and rails extending between the first flange and the second flange, wherein the drill guide assembly is mounted on the rails and moveable thereon.

According to a further aspect of the apparatus, the magnetic location sensors communicate location signals wirelessly with the position processor.

There is further provided according to embodiments of the invention a method, which is carried out by providing a shell conformable to a limb of a patient and a drill guide assembly movably mounted on the shell having a plurality of radiopaque markers affixed thereon. The method is further carried out by generating magnetic fields, and sensing the magnetic fields using a plurality of magnetic location sensors, transmitting signals from the magnetic location sensors to a position processor, and responsively to the signals computing with the position processor positional information of the magnetic location sensors and using the positional information to place the markers in registration with an anatomical image.

BRIEF DESCRIPTION OF THE SEVERAL VIEWS OF THE DRAWINGS

For a better understanding of the invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the invention. It will be apparent to one skilled in the art, however, that not all these details are necessarily needed for practicing the invention. In this instance, well-known circuits, control logic, and the details of computer program instructions for conventional algorithms and processes have not been shown in detail in order not to obscure the general concepts unnecessarily.

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

The terms "link", "links", "couple" and "couples" are intended to mean either an indirect or direct connection. Thus, if a first device couples to a second device, that connection may be through a direct connection, or through an indirect connection via other devices and connections.

Figure 1:
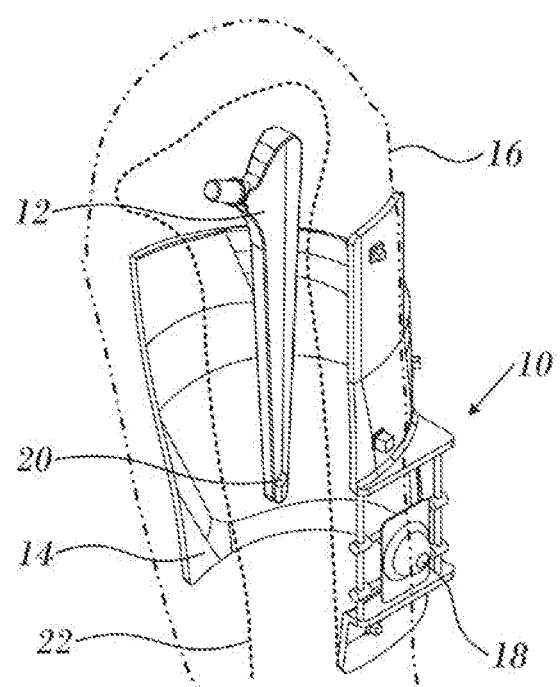
FIG. 1 is a schematic view of a jig for aligning a drill bushing with a transverse bore of a femoral nail accordance with an embodiment of the invention.

Turning now to the drawings, reference is initially made to FIG. 1, which is a schematic view of a jig 10 for intraoperatively aligning a drill guide or bushing with a transverse bore of an intramedullary femoral nail 12 in accordance with an embodiment of the invention. The jig 10 has a semi-rigid shell 14, which, in an operative position of the jig 10, partially encircles a limb of a patient, such as thigh 16 in order to stabilize the jig 10. The jig 10 is provided with a movable drill guide 18 that can be manipulated to align with a transverse bore 20 in the distal portion of the femoral nail 12. When properly aligned, a locking screw (not shown) can be inserted through cortex of femur 22 and into the bore 20 to stabilize the femoral nail 12. The components of the jig 10 are mostly non-metallic and radiolucent, for example plastic.

Figure 2:
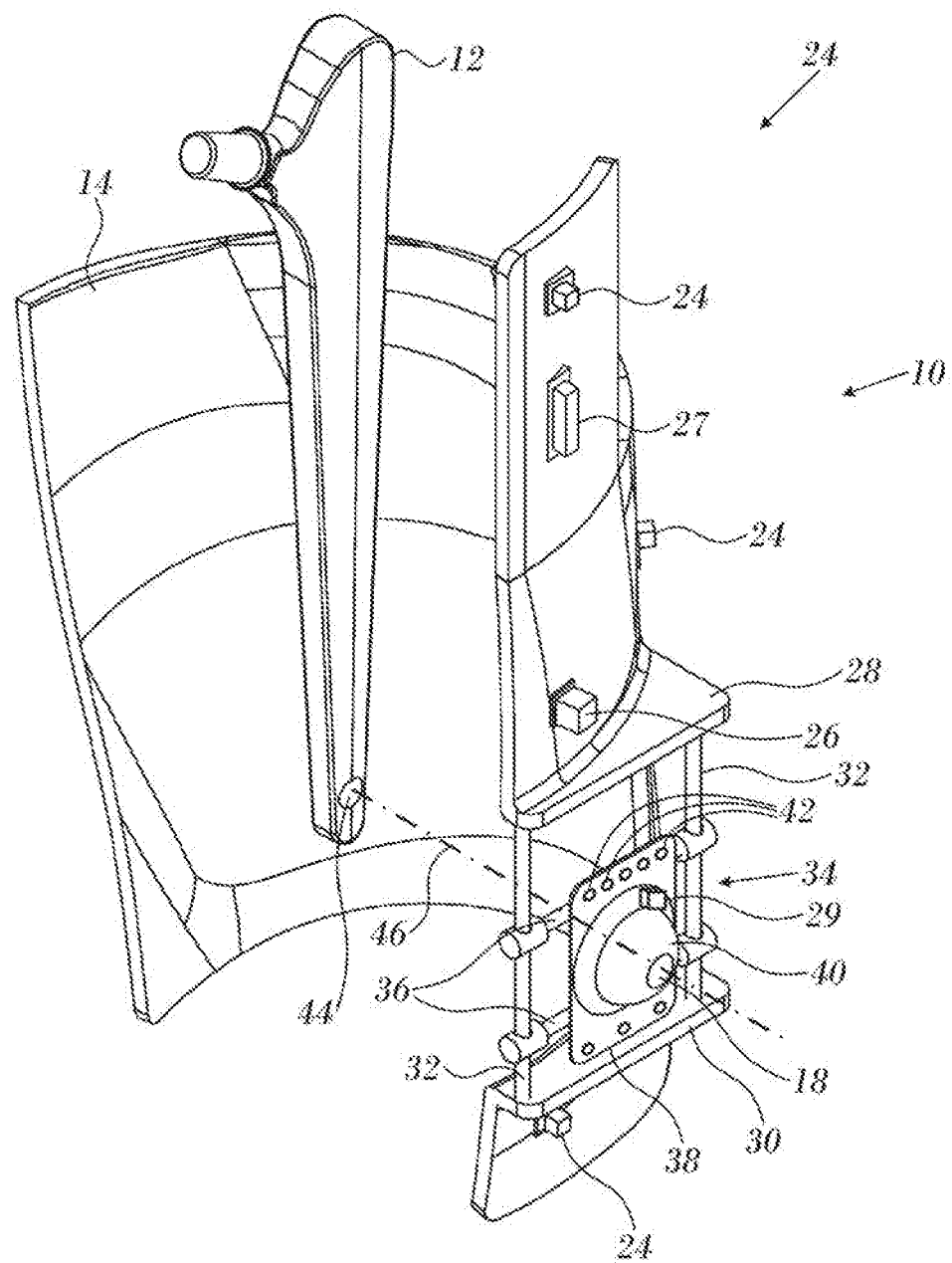
FIG. 2 is an oblique elevation of the jig shown in FIG. 1 in accordance with an embodiment of the invention.

Reference is now made to FIG. 2, which is an oblique elevation of jig 10, schematically showing an operative relationship to femoral nail 12 in accordance with an embodiment of the invention. A plurality of magnetic sensors 24 are distributed on shell 14. Three sensors 24 are visible in FIG. 2, and are sufficient to provide location information needed to position the drill guide 18. However more sensors may be provided, such as five sensors.

In this embodiment the sensors 24 are connected to processing unit 27, and to a transmitter 26, which may be integral with or separate from the processing unit 27, all embedded in the shell 14. The transmitter 26 (or the processing unit 27 itself) contains three magnetic field generators, which operate under control of the processing unit 27. In addition to the embodiments of the field generators that are described below, many other configurations are possible, including flat coils and other geometric arrangements. The magnetic fields produced are sensed by sensors 24. The processing unit 27 is configured to read the sensors 24 and obtain the location and orientation of the jig with respect to fluoroscopic images as described below. The processing unit 27 produces location and attitude information that is presented to the operator, typically via a console and display monitor, such as in the example shown below in FIG. 5.

Flanges 28, 30 are connected by rails 32 that are oriented generally parallel to the femur and the femoral nail 12 when in an operating position. A drill guide assembly 34 is mounted on the rails 32 and is slidable on the rails 32 generally between proximal and distal extremes. The assembly 34 comprises parallel struts 36 that are transverse to the rails 32. In this embodiment the rails 32 pass through transverse bores in the struts 36.

The struts 36 support a plate 38 that is connected with a ball joint 40 having drill guide 18 tunneled therethrough. Multiple radiopaque markers, x-ray fiducials 42, are distributed on the plate 38. The ball joint 40 allows free rotation of the drill guide 18 but does not allow translation. Sensor 29, located on the ball joint 40 provides the orientation of the drill guide 18 to the operator. Sensor 29 is also linked to the processing unit 27.

Translation generally parallel to the femoral nail 12 is achieved by movement of the assembly 34 along the rails 32. The jig 10 can be rotated generally about the longitudinal axis of the femoral nail 12 by slipping the shell 14 about the leg of the patient. Other mechanical arrangements for targeting the nail hole known in the art may be substituted for the ball joint 40.

Combinations of the above-described motions provide 3-dimensional alignment with the axes of with a transverse bore 44 located near the distal end of femoral nail 12 and the drill guide 18. When the drill guide 18 is in axial and positional alignment (indicated by broken line 46) with the bore 44, a locking screw can be inserted through the cortex of the patient's femur to stabilize the position of the femoral nail 12 with respect to the femur. Surgical access to the bore 44 can be obtained by means of a drilling operation in which a drill bit (not shown) is directed through the drill guide 18.

Figure 3:
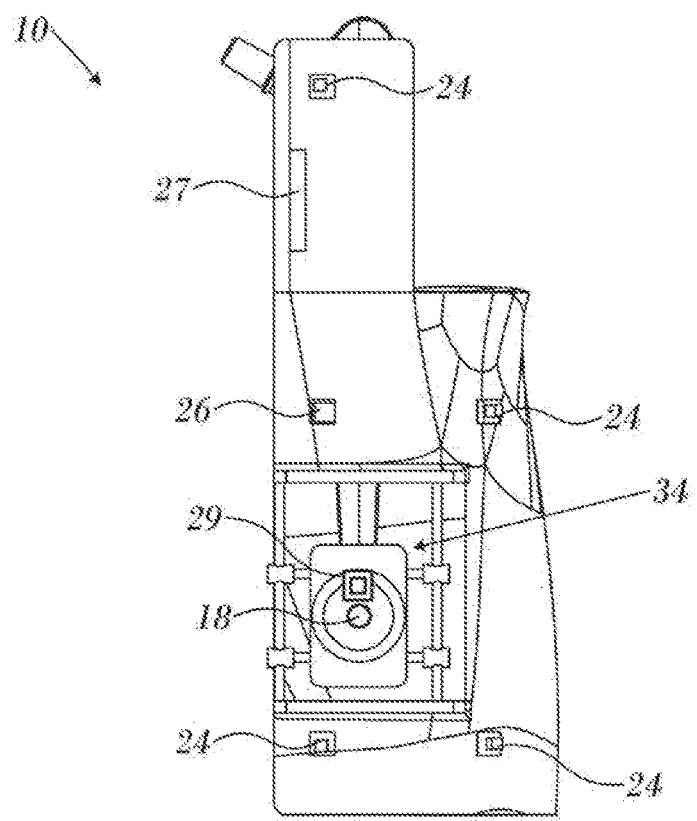
FIG. 3 is an elevation of the jig shown in FIG. 1 in accordance with an embodiment of the invention.
Figure 4:
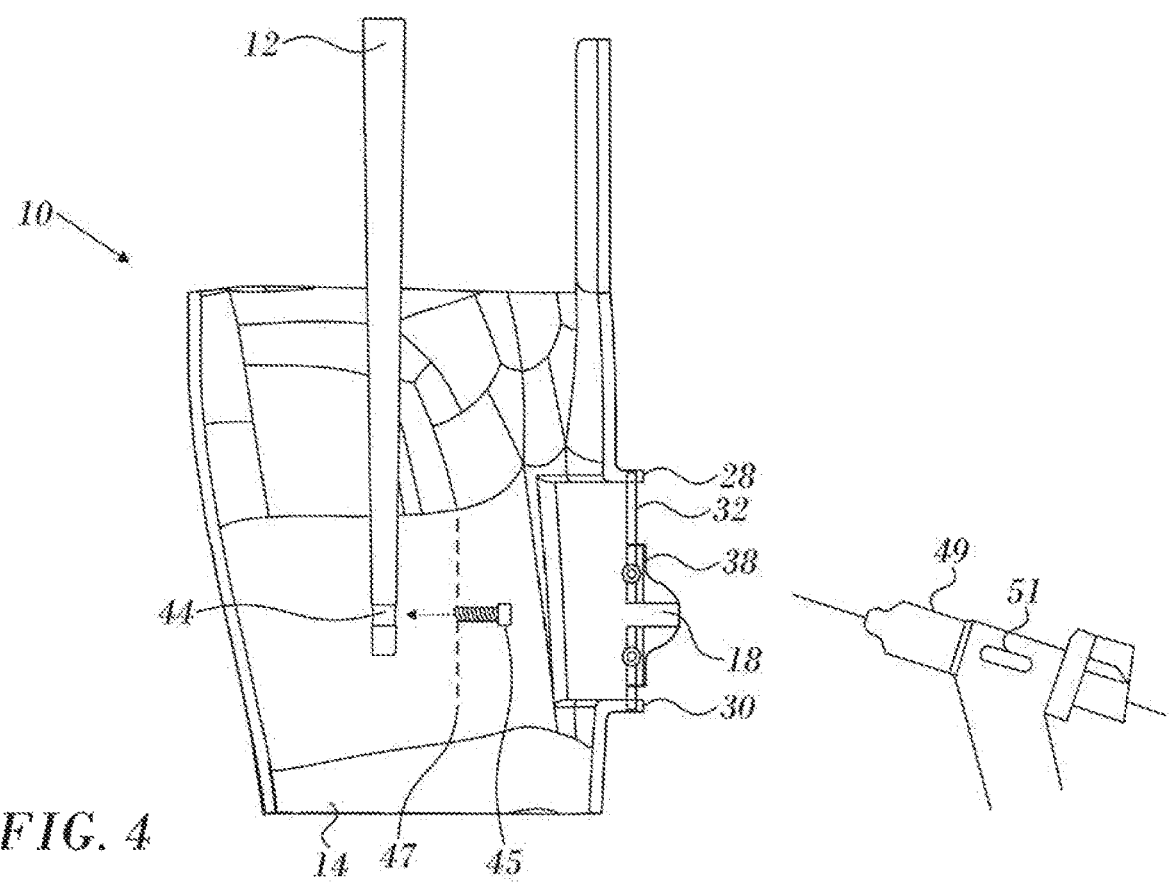
FIG. 4 is a partially schematic sectional view through the jig shown in FIG. 1 showing a femoral nail and locking screw in accordance with an embodiment of the invention.

Reference is now made to FIG. 3, which is an elevation of jig 10 in accordance with an embodiment of the invention. In this view the assembly 34 is seen along the axis of drill guide 18. FIG. 4 is a partially schematic sectional view through the jig 10 taken through the bore 44 of the femoral nail 12 and through the drill guide 18. A locking screw 45 is shown in relation to cortex 47 in alignment with the bore 44 and the drill guide 18. Prior to inserting the screw 45, the cortex 47 is drilled using a surgical drill 49 that includes a magnetic sensor 51. Using the magnetic sensor 51 the coordinates of the drill bit can be established by a position processor in the same frame of reference as the bore 44. The depth of the bore 44 is known, as well as its attitude in the frame of reference, enabling the operator (or a robot) to guide the drill bit through the drill guide 18 directly to the bore 44 in alignment with the axis of the bore 44. Thereafter the screw 45 may be driven into the bore 44, locking its position to the cortex 47. The magnetic sensor 51 may be linked to the processor wirelessly or by cable, as described in the embodiments below.

Figure 5:
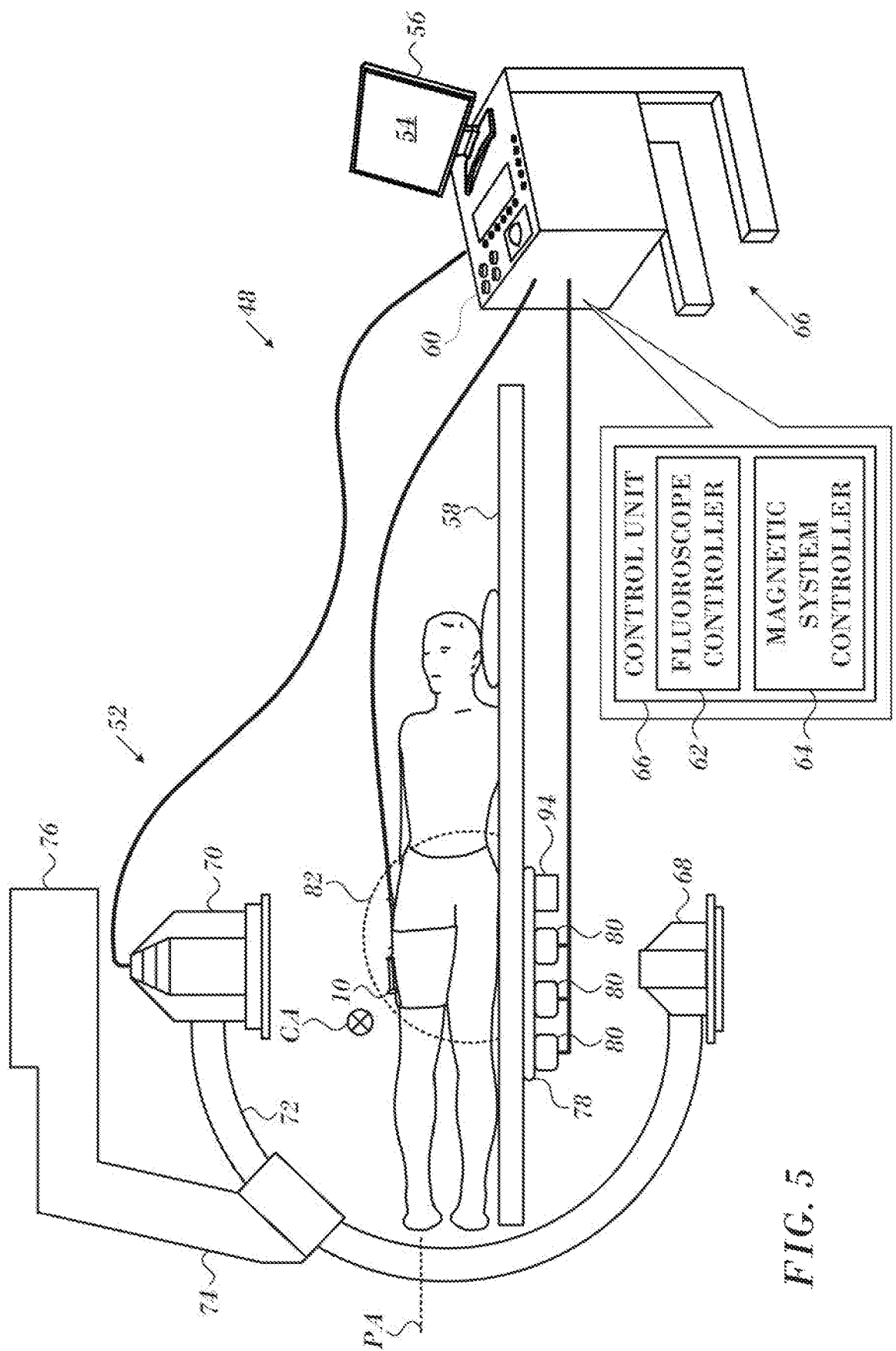
FIG. 5 is a schematic diagram illustrating a fluoroscopic image and magnetic mapping integration system according to an embodiment of the invention.

Reference is now made to FIG. 5, which is a schematic diagram illustrating a fluoroscopic image and magnetic mapping integration system 48 according to an embodiment of the invention. System 48 combines a three-dimensional map of a body organ such as a leg that is acquired by a magnetic tracking system 50, with a two-dimensional fluoroscopic image of the patient acquired by a fluoroscope 52, so forming a combined display 54 that is presented to an operator of system 48 on a screen 56. The patient is assumed to be lying on a table 58 of system 48, and magnetic tracking system 50 and fluoroscope 52 acquire the 3-dimensional map and 2-dimensional image of the patient, as described in more detail below. The 2-dimensional image acquired by the fluoroscope may be of the femur of the patient, and the body organ mapped by the magnetic tracking system may comprise a hip and thigh of the patient.

While in practice tracking system 50 and fluoroscope 52 may typically be configured as separate physical units with separate control units, in the present description, for simplicity, system 48 is assumed to be operated by a single control unit 60.

Control unit 60 comprises a fluoroscope controller 62 operating the fluoroscope, and a magnetic system controller 64 operating the magnetic tracking system, and the unit is under overall control of a system processor 66, the processor, inter alia, generating combined display 54 on screen 56. Software for processor 66 may be downloaded to the processor in electronic form, over a network, for example, or it may, alternatively or additionally, be provided and/or stored on non-transitory tangible computer-readable media, such as magnetic, optical, or electronic memory.

Fluoroscope 52 comprises an X-ray source 68 and a detector 70, the radiator and detector being mounted on opposite ends of a C-arm 72, assumed herein to comprise an arc of a circle. C-arm 72 is typically held at a lower end 74 of an L-arm 76, the L-arm being attached at its upper end to a ceiling of an operating theater, or at its lower end to the operating theater floor. C-arm 72 may be rotated around a horizontal pivot axis PA, which in the diagram is in the plane of the paper. C-arm 72 may also rotate around a C-arm axis CA, which is perpendicular to the plane of the paper and which passes through the center of the C-arm circle. Nominally, the two axes intersect at the C-arm center of rotation, also termed the iso-center, and are orthogonal to each other. The operator of system 48 is able to adjust rotations of fluoroscope 52 about axes PA and CA, as well as other geometrical parameters of the fluoroscope, using fluoroscope controller 62.

Magnetic tracking system 50 comprises a location pad 78, which typically has three sets 80 of generally similar coils fixedly mounted. The mount can be on the pad, as shown in FIG. 5. Each of the sets 80 of coils typically comprises three orthogonally oriented coils, so that there are a total of nine coils fixedly attached to location pad 78. Location pad 78 is fixedly attached to a jig, as described in further detail below. The coils, under control of magnetic system controller 64, transmit alternating magnetic fields into a region 82 in proximity to the pad and above the bed.

Suitable location pads for various types of applications requiring low-profile or miniature, or specialized embodiments are described in commonly assigned U.S. Patent Application Publication Nos. 20170007156, 20170007155, 20170079553, and 20150173643 all of which are herein incorporated by reference. When miniaturized versions are incorporated, as in transmitter 26 of the jig 10 (FIG. 2), the sets 80 can be omitted.

Figure 6:
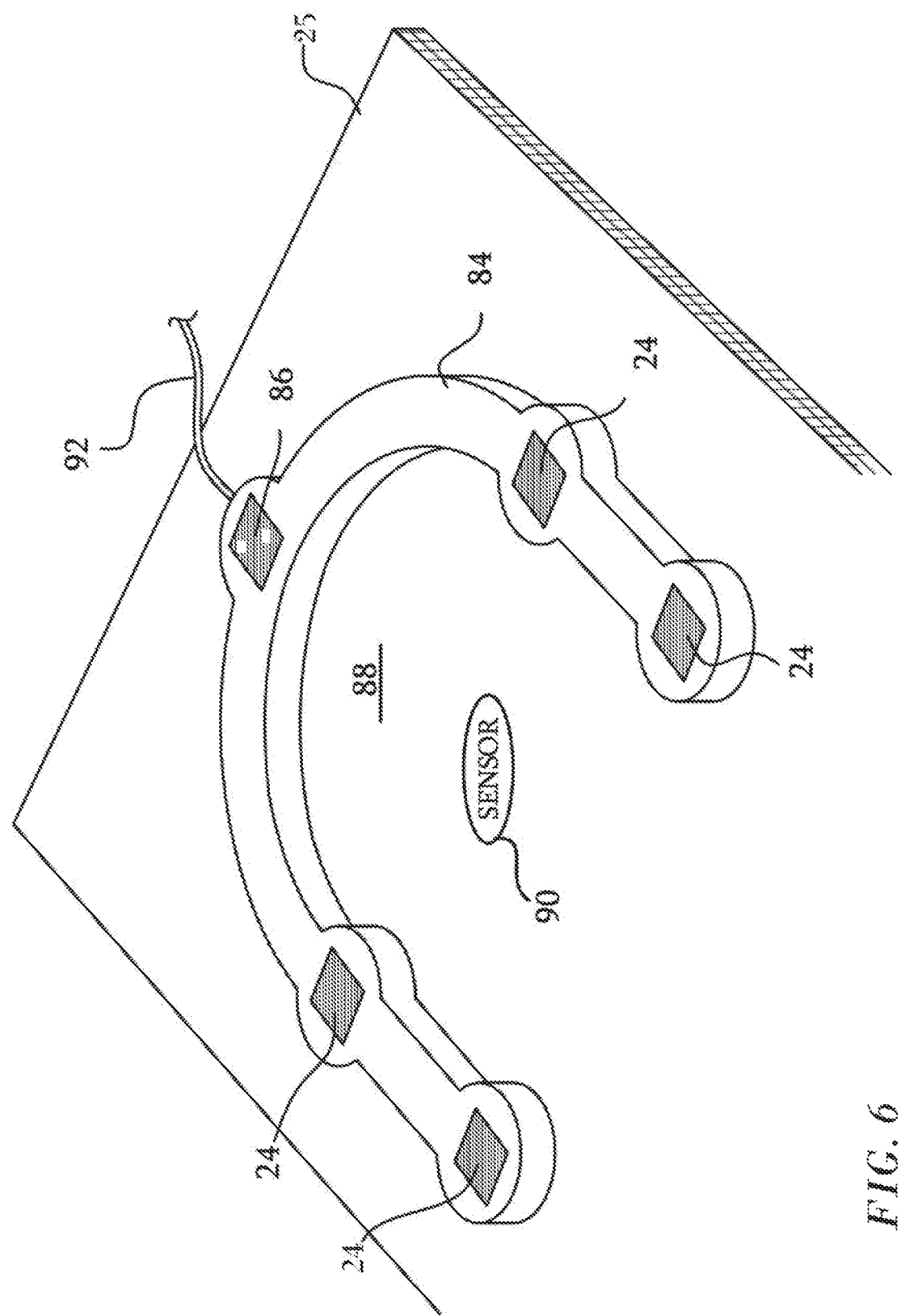
FIG. 6 is a location pad in accordance with an embodiment of the invention.

Reference is now made to FIG. 6, which is a location pad assembly 84, in accordance with an embodiment of the invention. Assembly 84 may be adapted to be incorporated onto a tool or jig, as described in the above noted U.S. Patent Application Publication No. 20170079553, and as further described hereinbelow. Assembly 84 comprises five magnetic field radiators 86, which by way of example are fixed in a horseshoe shaped frame. Radiators 86 are configured to radiate alternating magnetic fields at respective frequencies into a region 88, in proximity to assembly 84. The alternating magnetic fields induce signals in a sensor 90, typically a set of three orthogonal coils, and the signals may be analyzed to derive the location and orientation of the sensor with respect to assembly 84. It will be understood that the location and orientation of sensor 90 may be determined for substantially any positioning of the sensor within region 88.

Elements of assembly 84, including radiators 86, may be controlled by a system processor, such as processor 66 (FIG. 5), comprising a processing unit communicating with one or more memories. Typically, the elements may be connected by cables to the processor 66, for example, radiators 86 may be connected by a cable 92 to processor 66. Alternatively, or additionally, the elements may be coupled wirelessly to the processor 66.

Reverting to FIG. 5, in order to register the coordinate systems, or frames of reference, of magnetic tracking system 50 and fluoroscope system 52, system 48, in a calibration phase, uses one or more registration elements. A given registration element has the property that its location and orientation may be determined simultaneously in both coordinate systems. A registration procedure is normally undertaken prior to a patient session. Details are described in commonly assigned U.S. Patent Application Publication No. 20140114173 by Bar-Tal et al., entitled Integration Between 3-dimensional Maps and Fluoroscopic Images, which is herein incorporated by reference.

In addition to the magnetic tracking coordinate system and the fluoroscope coordinate system, referred to above, a coordinate system based on location pad 78, and one based on registration module 94, are present in system 48. These systems are used as intermediaries in the registration of the magnetic tracking and the fluoroscope coordinate systems.

Figure 7:
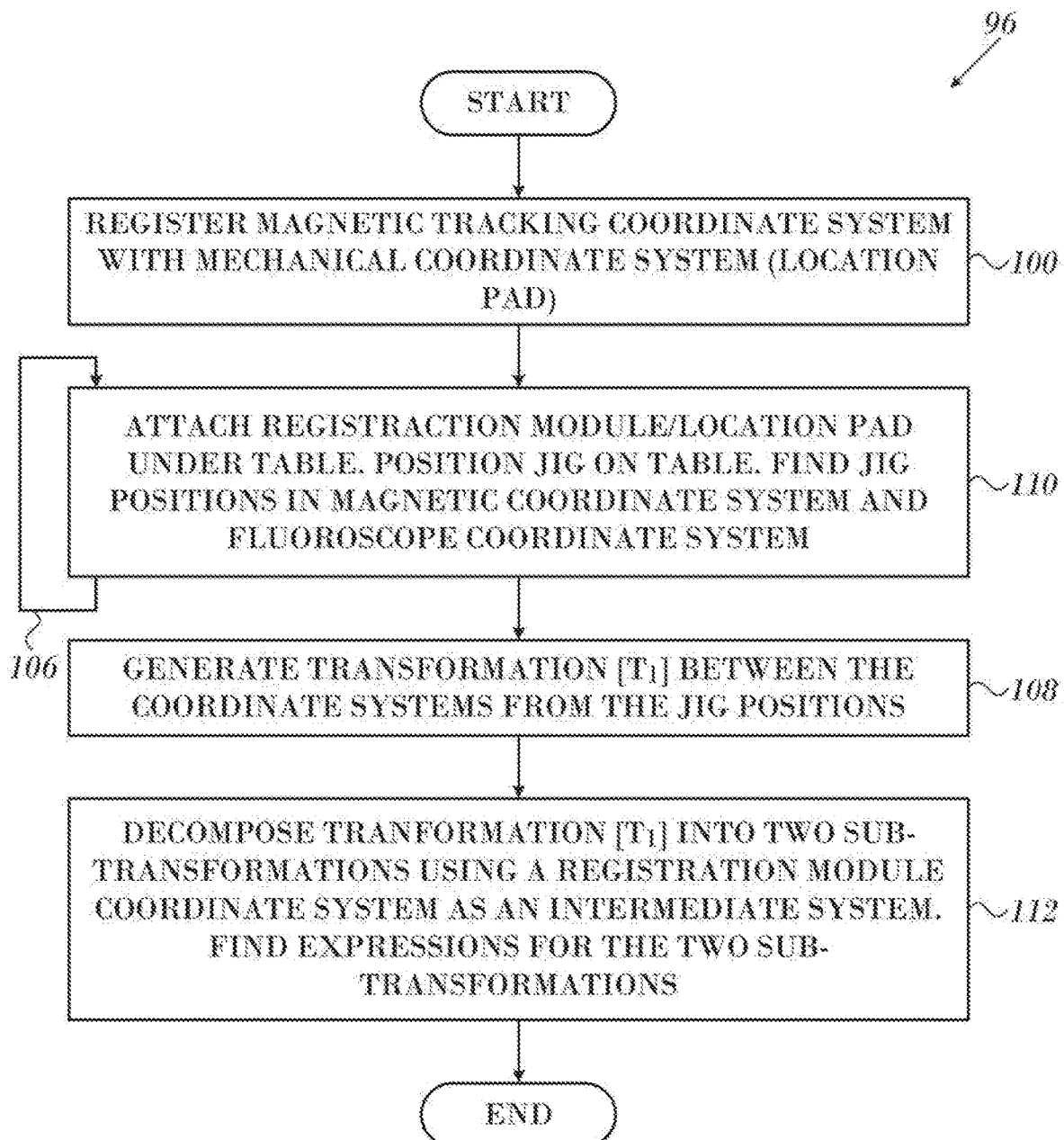
FIG. 7 is a flowchart of steps to register a magnetic tracking coordinate system with a fluoroscope coordinate system according to an embodiment of the invention.

FIG. 7 is a flowchart 96 of steps to register a magnetic tracking coordinate system with a fluoroscope coordinate system according to an embodiment of the invention. In the description of flowchart 96, it is assumed that the model relationship has been generated.

In an initial step 100, the magnetic tracking coordinate system is registered with a mechanical coordinate system defined by the mechanical structure of location pad 78, herein termed the location pad coordinate system. The registration is typically performed prior to installation of the location pad into system 48, and may be performed on production of the location pad. The registration typically involves defining a location pad coordinate system in terms of the locations of the three sets 80 of coils comprising the location pad, measuring the location and orientation of a sensor coil, typically in a jig or tool such as jig 10 (FIG. 2), with respect to the location pad coordinate system, and relating signals from the sensor coil to the measured location and orientation. The registration performed in this step is a nominal registration, and corrections may be made to this nominal registration in later steps of the flowchart.

Magnetic sensors 104 are fixed to jig 10, in their known locations and orientations, and the coils in the location pad are energized. Signals from the sensors, generated in response to the magnetic field radiated by the location pad coils, are received by magnetic system controller 64, and the controller analyzes the signals to determine a location and an orientation for the jig in the magnetic coordinate system.

Simultaneously, fluoroscope controller 62 analyzes the image acquired by detector 70 and, using the model generated in flowchart 98, determines a location and an orientation of jig 10 in the fluoroscope coordinate system.

Typically, as illustrated by an arrow 106, in step 110 jig 10 is moved into other positions, by moving the jig on table 58, and/or by moving table 58. For each new position of the jig, locations and orientations of the jig in both coordinate systems are determined by controllers 62, 64. The images acquired for the multiple jig positions of this step increase the accuracy of the transformation generated in the following step.

In a transformation generation step 108, system processor 66 receives the results of the locations and orientations of the jig in the two coordinate systems, in the multiple positions set in step 110. Processor 66 uses the results to generate a transformation [T1] between the two coordinate systems. Processor 66 may check the accuracy of transformation [T1], and adjust values of elements of the transformation, by using other magnetic sensors in known positions.

In a final step 112, processor 66 assumes that transformation [T1] is a composition of two sub-transformations, according to equation (1):

$$[T_{module,fluoro}] * [T_{magnetic,module}] = [T_1] \quad (1)$$

where $[T_{module,fluoro}]$ is a transformation between the fluoroscope coordinate system and a coordinate system defined by the registration module, and $[T_{magnetic,module}]$ is a transformation between the registration module coordinate system and the magnetic coordinate system.

The location and orientation of the registration module in the fluoroscope coordinate system are known from the images of the module acquired by detector 70, and these enable processor 66 to evaluate $[T_{module,fluoro}]$. While nominal location and orientation coordinates of the module in the magnetic coordinate system are known, (so that transformation $[T_{magnetic,module}]$ is nominally known) deviations from specification in the mounting of the registration module to the location pad cause deviations from the nominal values. Processor 66 consequently applies equation (1), where transformations $[T_1]$ and $[T_{module,fluoro}]$ are known, to find an actual expression for transformation $[T_{magnetic,module}]$. This expression is used in an operational phase of system 48, as is explained below.

Figure 8:
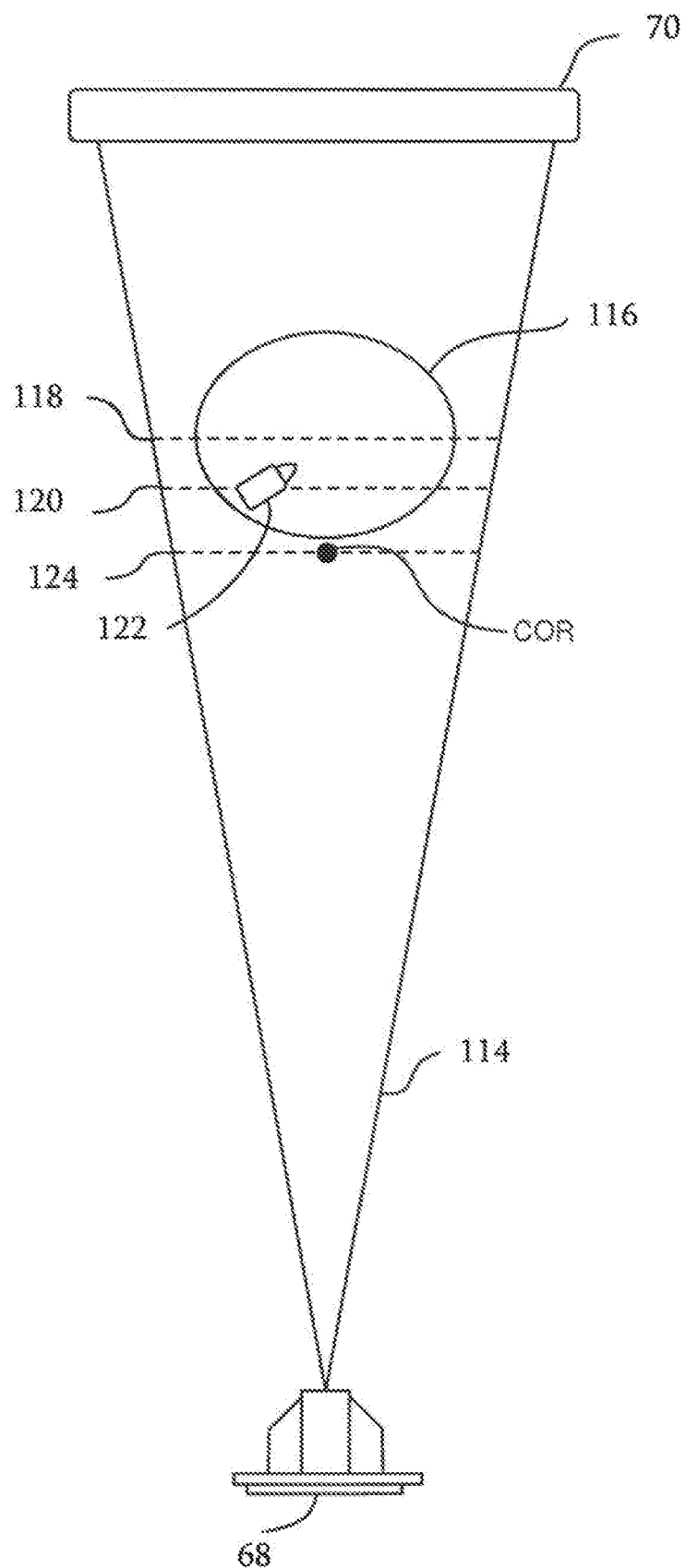
FIG. 8 is a schematic diagram illustrating methods for combining an image and a map according to an embodiment of the invention.

FIG. 8 is a schematic diagram illustrating methods for combining an image and a map according to an embodiment of the invention. Source 68 acts as a point source of X-rays, which radiate through a "pyramid" 114, so that in the fluoroscope system the 2-dimensional image acquired by detector 70 of a 3-dimensional volume of interest 116 in the pyramid corresponds to a perspective projection, where the source acts as the origin of the projection, and wherein projection lines (not shown on the diagram) radiate from the source to the detector. However, the 2-dimensional display of the 3-dimensional volume of interest, as presented in the magnetic system, is typically different from a perspective projection. For example, in the CARTO® 3 System, available from Biosense Webster, Inc., 3333 Diamond Canyon Road, Diamond Bar, Calif. 91765, wherein the volume of interest is the heart, a 3-dimensional electropotential map of the heart is typically provided on screen 56 as an orthographic projection, wherein projection lines through the heart are parallel to each other.

Embodiments of the invention allow an operator of system 48 to select an effective plane, parallel to detector 70, within pyramid 114, which is to be used for aligning and positioning the perspective projection in the fluoroscope system with the orthographic projection in the magnetic system. The plane selected is a plane within the 3-dimensional volume of interest. Three examples of the planes, assuming that the volume of interest corresponds to a heart electropotential map, are shown in the figure, although other planes may be used. A plane 118 is a plane through a center of gravity of the electropotential map; a plane 120 is a plane through an item of interest 122 in the map; and a plane 124 is a plane through a center of rotation COR of the fluoroscope system, as projected onto the map. Selection of the different planes is effected by deciding on a point in the image and in the map that is to correspond, and then adjusting a magnification of the perspective projection.

The magnetic system typically determines both the location and orientation of objects that are tracked by the system. An icon of the object may be used in the combined display presented on screen 56, and the icon image may be varied to represent both the location and orientation of the object.

The description above has assumed that the perspective projection of the fluoroscope system is incorporated into the orthographic projection of the magnetic system. However, the description may be applied, mutatis mutandis, to converting the orthographic projection of the magnetic system into a perspective projection. The perspective projection of the fluoroscope system may then be incorporated into the magnetic perspective projection.

Once transformation [T2] has been formulated, the transformation may be applied for substantially any display on screen 56 that is desired by the system operator. Furthermore, the transformation may be applied completely automatically for the chosen display, and may be applied to real-time imaging as well as to stored images.

Typically, processor 66 may import and store every image generated by the fluoroscope. The processor may then process the fluoroscopic image to derive the desired image plane coordinates (in the magnetic system), and store the image along with these coordinates. This image can then be viewed aligned and in overlay with the magnetic system map.

Similarly, when the operator rotates the magnetic system map to see a different view, and this view angle corresponds to a projection angle at which a fluoroscopic image was previously captured and stored, the processor may recall the corresponding image automatically and display it together with the map. Alternatively or additionally, if no fluoroscopic image has been acquired and stored at the current map viewing angle, processor 66 may automatically instruct the fluoroscope to acquire an image for display together with the magnetic system map at this angle.

As a further option, the operator can set the magnetic mapping system so that upon acquiring a fluoroscopic image at a certain angle (or displaying a previously-acquired image), processor 66 automatically rotates the magnetic system map so that the projection angle of the map matches that of the fluoroscopic image. This technique ensures that the magnetic system map projection and the fluoroscopic projection that are displayed at any time are in proper registration and helps to prevent operator errors in carrying out the procedure.

The technique described above can be used not only to import and register entire fluoroscopic images into the magnetic mapping system, but also to import and register particular objects—such as particular anatomical structures and features—that may be segmented in a fluoroscopic image. Based on registration of the fluoroscopic image from which the object is taken, each such object will have a location and orientation in the magnetic coordinate system. An object selected by the user can thus be registered and superimposed on the magnetic map with little or no user involvement in the actual registration process.

The processor can also invert the fluoroscopic image by 180°. For example, when the fluoroscopic image is taken in HFS view, and the orientation of the magnetic system map is also HFS, the fluoroscopic image may be displayed on the magnetic system map. If the magnetic system map orientation is inverted, on the other hand, the processor can invert the fluoroscopic image from the HFS view, and thus continue to display the fluoroscopic image in proper registration with the magnetic system image. In treating atrial fibrillation, for example, the operator usually sets the magnetic system orientation inverted from the HFS view, in order to see the veins while ablating. With the inverted view, the operator will also be able to see also the fluoroscopic image in the inverted view, even when the fluoroscope itself is unable to actually capture images in this orientation.

The ability of the system to register fluoroscopic images with the magnetic system map, and to present correctly the appropriate fluoroscopic image at each angle of projection of the magnetic system map, can be used in various other ways to enhance visualization during medical procedures. For example, the magnetic system map may be rotated and corresponding fluoroscopic images may be displayed in order to enable the operator to verify an alignment between an anatomical feature and an object being manipulated.

Fluoroscopic images that have been registered with the magnetic system map can also be used to assist in aligning and registering other images, such as CT (computerized tomography) or MRI (magnetic resonance imaging) images, with the magnetic system map.

Registration of fluoroscopic images with magnetic maps in the manner described above can be useful in reducing the X-Ray dosage to which patients are exposed. For example, the operator may be able to carry out medical procedures without simultaneous X-Ray imaging by using pre-acquired, registered fluoroscopic images. Similarly, a pair of pre-acquired, registered fluoroscopic images from different angles can be used to assist the operator in manipulating an object at a certain location (such as the femur) based on the magnetic map without requiring simultaneous X-Ray imaging. Fluoroscopic cine loops can also be registered in the manner described above and then played back in proper registration during magnetic mapping and treatment.

Figure 9:
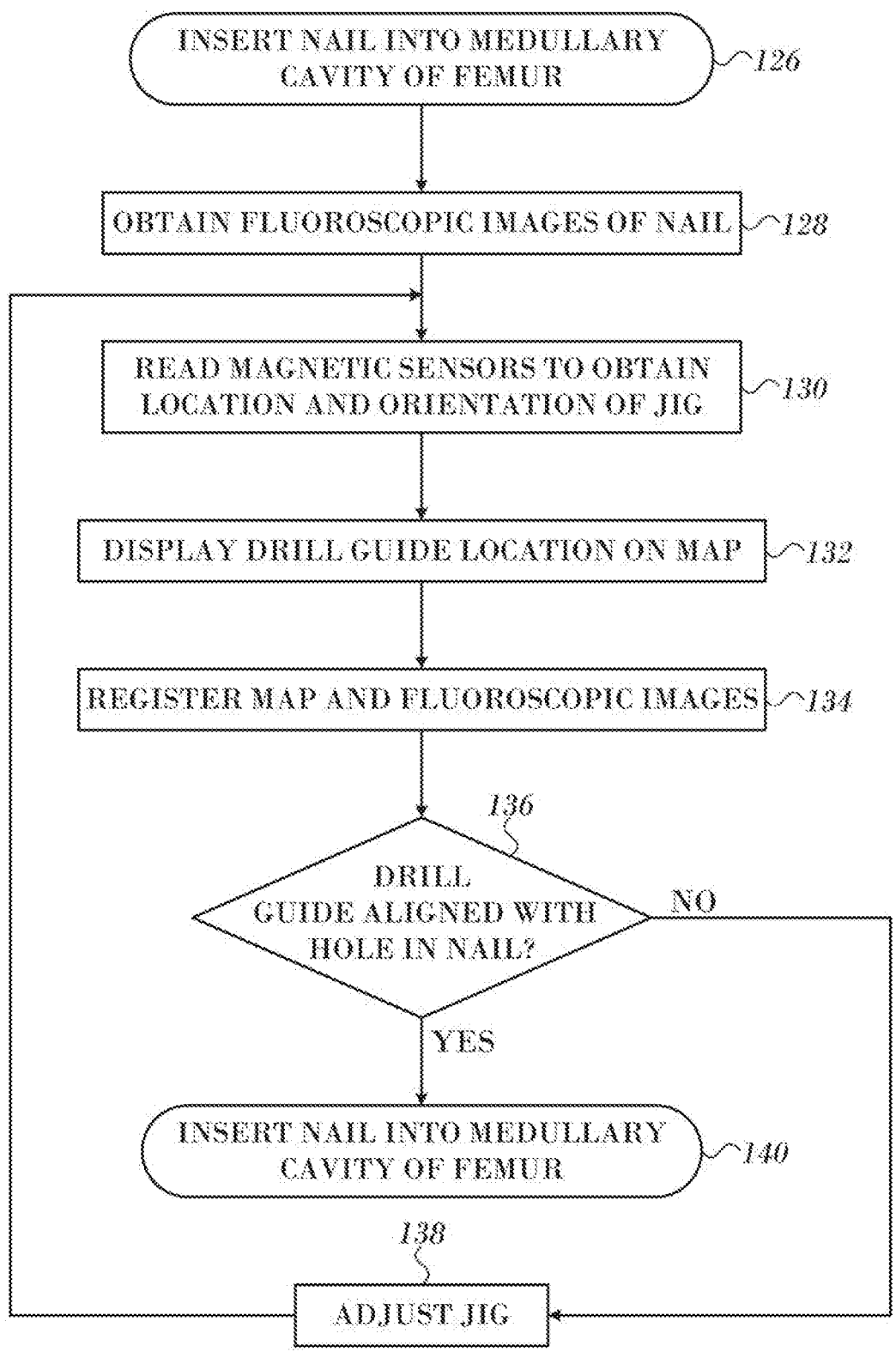
FIG. 9 is a flow chart of a method of placing a locking screw in a femoral nail in accordance with an embodiment of the invention.

Reference is now made to FIG. 9, which is a flow chart of a method of placing a locking screw in a femoral nail in accordance with an embodiment of the invention. The process steps are shown in a particular linear sequence for clarity of presentation. However, it will be evident that many of them can be performed in parallel, asynchronously, or in different orders. Those skilled in the art will also appreciate that a process could alternatively be represented as a number of interrelated states or events, e.g., in a state diagram. Moreover, not all illustrated process steps may be required to implement the method. At initial step 126 a femoral nail is placed operatively in a conventional manner.

Next, at step 128 fluoroscopic images of the nail are taken. Generally, two orthogonal images are obtained.

Figure 10:
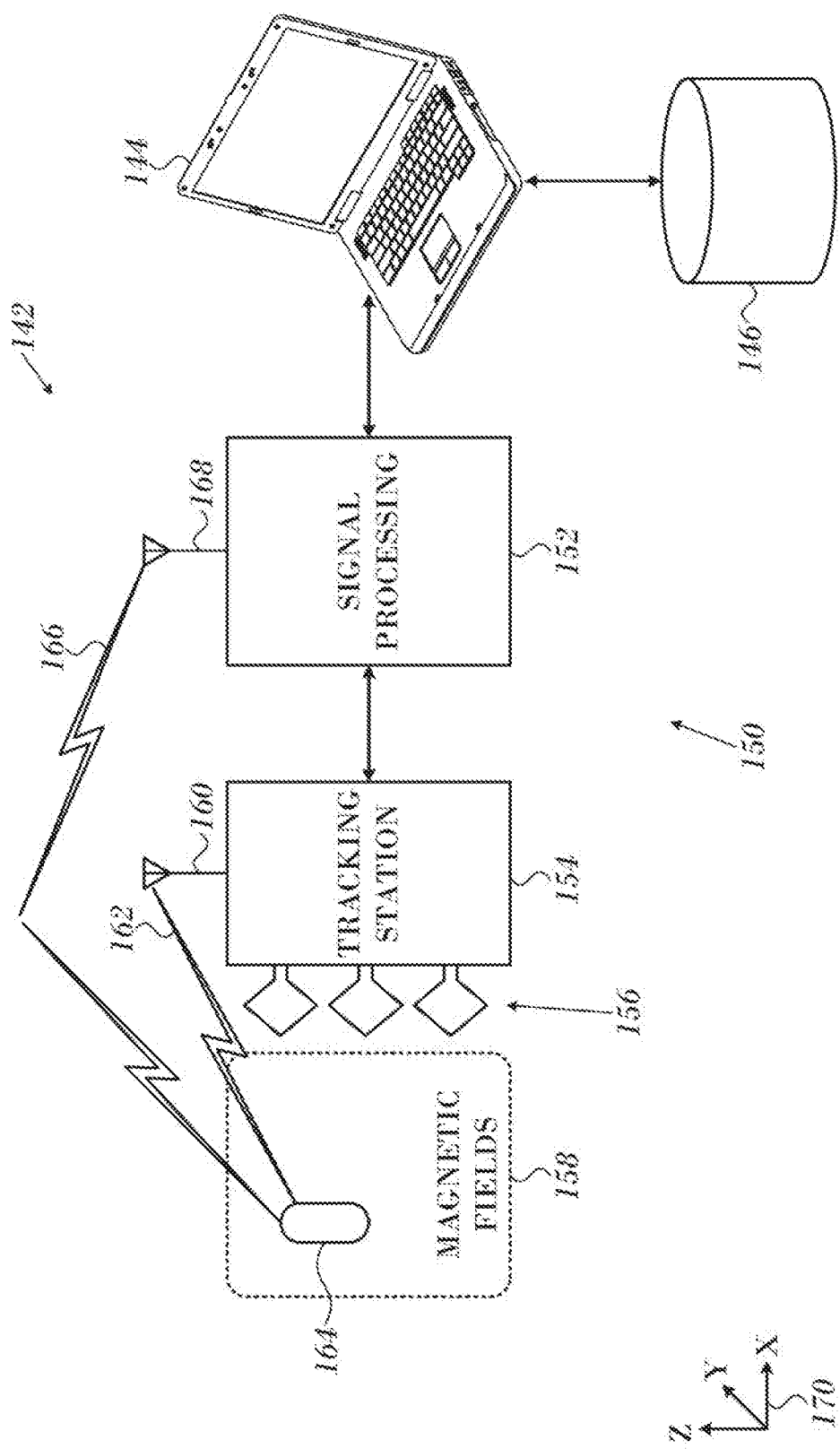
FIG. 10 is a block diagram of an orthopedic monitoring system in accordance with an alternate embodiment of the invention.

Next, at step 130 readings are taken from the magnetic sensors on the jig and the location of the drill guide obtained. Next, at step 132 the location of the drill guide, such as the drill guide 18 (FIG. 2), is displayed on a map, using a monitoring system such as the system 48 (FIG. 5) or system 142 (FIG. 10).

At step 134 the map prepared in step 132 is placed in registration with the fluoroscopic images obtained in step 128 and displayed for the operator. The details of registering the images are presented in FIG. 7 and FIG. 8 and the discussion thereof.

Next, at decision step 136, it is determined if the drill guide is aligned with the bore at the distal end of the femoral nail. If the determination at decision step 136 is negative, then control proceeds to step 138. As explained above, the jig is capable of translational motion generally parallel to the femoral nail, and rotational motion in a plane transverse to the nail. The axis of the drill guide with respect to the axis of the bore of the femoral nail is adjustable using by manipulating the ball joint 40 (FIG. 2). Normally the operator manually performs the adjustment. In some embodiments servomechanisms (not shown) may be linked to the assembly 34 and the jig 10 and the adjustment operation performed automatically, using known robotic methods. Necessary adjustments to the processor 66 (FIG. 5) will be apparent to those skilled in the art of robotics, and are not discussed herein.

After performing step 138 control returns to step 130 to prepare another map. Normally it is not required to repeat the fluoroscopic imaging, which minimizes radiation exposure to the patient.

If the determination at decision step 136 is affirmative, then control proceeds to final step 140. The femoral cortex may be surgically exposed using the drill guide, and the locking screw inserted into the bore in the femoral nail.

Alternate Embodiment

Reference is now made to FIG. 10, which is a block diagram of an orthopedic monitoring system 142 in accordance with an alternate embodiment of the invention. The monitoring system includes wireless tracking functionality. The functionality is generally implemented cooperatively with a computer 144 carrying out various data processing operations on implant and/or positional data items, and other data items, stored in database 146. In one embodiment computer 144 and database 146 provide an orthopedic assessment sub-system for the implantation of a femoral prosthesis. The positional data items are obtained by wirelessly tracking markers. A wireless tracking sub-system 150 is provided by computer 144, positional signal processing circuitry 152 and tracking station 154.

Tracking station 154 includes three magnetic field generator coils 156. The three field generator coils 156 generate magnetic fields 158, which extends over a working volume of the tracking station. The tracking station also includes an antenna 160, which wirelessly transmits an electrical power signal 162 at a radiofrequency to a transponder 164 located within the working volume. Magnetic field transponder 164 wirelessly transmits a signal 166 in which is digitally encoded the position and orientation of the marker and also a unique identifier for the marker. The signal 166 is received by an antenna 168 in communication with the positional signal processing circuitry 152.

A suitable transponder 164 and associated tracking sub-system 150 for use in the orthopedic monitoring system 142 will briefly be described in greater detail. Aspects of the transponder 164 and tracking sub-system 150 are described in greater detail in U.S. Patent Application Publication No. US 2003/0120150, which is herein incorporated herein by reference.

The transponder 164, such as a wireless position sensor, which can be tracked by the tracking sub-system 142, has a housing. As explained above, the transponder 164 generates and wirelessly transmits a digital signal 166 encoding data items indicative of the marker's location (x, y and z coordinates within a Cartesian reference frame 170 of the tracking system) and orientation (pitch, roll and yaw), in response to the external magnetic fields 158 produced by the three field generator coils 156.

Circuitry is present in the tracking station 154 and additionally in positional signal processing circuitry 152. The field generator coils 156 are driven by driver circuits to generate electromagnetic fields at different, respective sets of frequencies $\{w_1\}$, $\{w_2\}$ and $\{w_3\}$. The sets of frequencies at which the coils radiate are set by the computer 144, which serves as the system controller for tracking sub-system 150. The respective sets of frequencies may all include the same frequencies, or they may include different frequencies. In any case, computer 144 controls driver circuits according to a known multiplexing pattern, which provides that at any point in time, no more than one field generator coil is radiating at any given frequency. Typically, each driver circuit is controlled to scan cyclically over time through the frequencies in its respective set. Alternatively, each driver circuit may drive a respective one of field generator coils 156 to radiate at multiple frequencies simultaneously.

For the purposes of system tracking station 154, field generator coils 156 may be arranged in any convenient position and orientation, so long as they are fixed in respect to some reference frame, and so long as they are non-overlapping, that is, there are no two field generator coils with the exact, identical location and orientation. Typically, for surgical applications the coils are located in a triangular arrangement. The coil axes may be parallel, or they may alternatively be inclined. Bar-shaped transmitters or even triangular or square-shaped coils could also be useful for such applications.

In orthopedic and other surgical applications, it is desirable that field generator coils 156 be positioned away from the surgical field, so as not to interfere with the surgeon's freedom of movement. On the other hand, the coils should be positioned so that the working volume of the magnetic fields 158 of the tracking system includes the entire area in which the surgeon is operating. At the same time, the locations and orientations of field generator coils 156 should be known relative to a given reference frame in order to permit the coordinates of transponder 164 to be determined in that reference frame. In practice, field generator coils 156 are mounted on a reference structure part of the tracking station 154.

The transponder 164 include sensor coils, in which electrical currents are induced to flow in response to the magnetic fields produced by field generator coils 156. The sensor coils may be wound on either air cores or cores of magnetic material. Typically, each marker comprises three sensor coils, having mutually orthogonal axes, one of which is conveniently aligned with a principal axis of the housing or of an orthopedic implant, such as a longitudinal axis. The three coils may be concentrically wound on a single core, or alternatively, the coils may be non-concentrically wound on separate cores, and spaced along the principal axis. The use of non-concentric coils is described, for example, in PCT Patent Publication WO 96/05768 and in the corresponding U.S. Pat. No. 6,690,963 filed on Feb. 10, 2004, which are incorporated herein by reference.

Alternatively, the transponder 164 may comprise only a single sensor coil or two sensor coils, in which case a plurality of transponders oriented in different directions may be required to assure sufficient precision. Further alternatively, transponder 164 may comprise magnetic position sensors based on sensing elements of other types known in the art, such as Hall effect sensors.

At any instant in time, the currents induced in the sensor coils comprise components at the specific frequencies in sets $\{w_1\}$, $\{w_2\}$ and $\{w_3\}$ generated by field generator coils 156. The respective amplitudes of these currents (or alternatively, of time-varying voltages that may be measured across the sensor coils) are dependent on the location and orientation of the transponder 164 relative to the locations and orientations of the field generator coils 156. In response to the induced currents or voltages, signal processing and transmitter circuitry in one or more instances of the transponder 164 generate and transmit signal 166 that is indicative of the location and orientation of the instances. These signals are received by receiving antenna 168, which is coupled to computer 144 via signal receiver and demodulation circuitry. The computer processes the received signals, together with a representation of the signals used to drive the field generator coils, in order to calculate location and orientation coordinates of the transponder 164. The coordinates are processed and stored by the computer 144 as will be described in greater detail below.

Although tracking sub-system 150 is described as comprising three field generator coils 156, in other embodiments, different numbers, types and configurations of field generators and sensors may used. A fixed frame of reference may be established, for example, using only two non-overlapping field generator coils to generate distinguishable magnetic fields. Two non-parallel sensor coils may be used to measure the magnetic field flux due to the field generator coils, in order to determine six location and orientation coordinates (x, y, z directions and pitch, yaw and roll orientations) of the sensor. Using three field generator coils and three sensor coils, however, tends to improve the accuracy and reliability of the position measurement.

Alternatively, if only a single sensor coil is used, computer 144 can still determine five position and orientation coordinates (X, Y, Z directions and pitch and yaw orientations). Specific features and functions of a single coil system (also referred to as a single axis system) are described in U.S. Pat. No. 6,484,118, whose disclosure is incorporated herein by reference.

When a metal or other magnetically-responsive article is brought into the vicinity of an object being tracked, the magnetic fields in this vicinity are distorted. There can be a substantial amount of conductive and permeable material in a surgical environment, including basic and ancillary equipment (operating tables, carts, movable lamps, etc.), as well as invasive surgery apparatus (scalpels, scissors, etc.). The magnetic fields produced by field generator coils 156 may generate eddy currents in such articles, and the eddy currents then cause a parasitic magnetic field to be radiated. Such parasitic fields and other types of distortion can lead to errors in determining the position of the object being tracked.

In order to alleviate this problem, the elements of the tracking station 154 and other articles used in the vicinity of the tracking sub-system 150 are typically made of non-metallic materials when possible, or of metallic materials with low permeability and conductivity. In addition, computer 144 may be programmed to detect and compensate for the effects of metal objects in the vicinity of the tracking station 154. Exemplary methods for such detection and compensation are described in U.S. Pat. Nos. 6,147,480 and 6,373,240, as well as in U.S. Pat. Nos. 7,974,680 and 7,321,228, which are incorporated herein by reference.

The marker in this embodiment comprises three sets of coils: sensor coils, power coils, and a communication coil. Alternatively, the functions of the power and communication coils may be combined, as described in U.S. Pat. No. 7,729,742, which is herein incorporated by reference. The coils are coupled to electronic processing circuitry, which is mounted on a suitable substrate, such as a flexible printed circuit board (PCB). Details of the construction and operation of the circuitry are described in the above-noted U.S. Pat. No. 7,729,742 and in U.S. Pat. No. 7,397,364, which is incorporated herein by reference in their entirety for all purposes.

Transponder 164 can include only a single sensor coil and a single power coil, but in practice transponder 164 typically comprises multiple coils of each type, such as three sensor coils and three power coils. The sensor coils are wound together, in mutually-orthogonal directions, on a sensor core, while the power coils are wound together, in mutually-orthogonal directions, on a power core. Alternatively, the sensor and power coils may be overlapped on the same core, as described, for example in U.S. Pat. No. 6,995,729, whose disclosure is incorporated herein by reference. It is generally desirable to separate the coils one from another by means of a dielectric layer (or by interleaving the power and sensor coils when a common core is used for both) in order to reduce parasitic capacitance between the coils.

In operation, power coils serve as a power source for transponder 164. The power coils receive energy by inductive coupling from external driving antenna 160 attached to RF power driving circuitry. Typically, the driving antenna radiates an intense electromagnetic field at a relatively high radio frequency (RF), such as in the range of 13.5 MHz. The driving field causes currents to flow in power coils, which are rectified in order to power the circuitry. Meanwhile, field generator coils 156 induce time-varying signal voltages to develop across the sensor coils as described above. The circuitry senses the signal voltages, and generates output signals in response thereto. The output signals may be either analog or digital in form. The circuitry drives the communication coil to transmit the output signals to receiving antenna 168 outside the patient's body. Typically, the output signals are transmitted at still higher radio frequencies, such as frequencies in the range of 43 MHz or 915 MHz, using a frequency-modulation scheme, for example. Additionally or alternatively, the coil may be used to receive control signals, such as a clock signal, from a transmitting antenna (not shown) outside the patient's body.

As explained above, the driver circuitry also comprises an RF power driver, which drives antenna 160 to emit power signal 162, preferably in the 2-10 MHz range. The power signal causes a current to flow in power coil, which is rectified by circuitry and used to power the markers internal circuits. Meanwhile, the electromagnetic fields produced by field generator coils 156 cause currents to flow in the sensor coil. This current has frequency components at the same frequencies as the driving currents flowing through the field generator coils 156. The current components are proportional to the strengths of the components of the respective magnetic fields produced by the generator coils in a direction parallel to the sensor coil axes. Thus, the amplitudes of the currents indicate the position and orientation of the sensor coils relative to field generator coils 156.

The circuitry measures the currents flowing in the sensor coils of the transponder 164 at the different field frequencies. It encodes this measurement in a high-frequency signal, which it then transmits back via an antenna to antenna 168. The circuitry comprises a sampling circuit and analog/digital (A/D) converter, which digitizes the amplitude of the current flowing in the sensor coils. In this case, the circuitry generates a digitally-modulated signal, and RF-modulates the signal for transmission by the antenna. Any suitable method of digital encoding and modulation may be used for this purpose. The circuitry also stores a unique identifier for each marker and similarly generates a digitally-modulated signal, and RF-modulates the signal 166 for transmission by the antenna. Other methods of signal processing and modulation will be apparent to those skilled in the art.

The digitally-modulated signal transmitted by the antenna is picked up by a receiver, coupled to antenna 168. The receiver demodulates the signal to generate a suitable input to signal processing circuits, which can be separate to, or integrated in, the computer 144. Typically, the receiver amplifies, filters and digitizes the signals from transponder 164. The digitized signals are received and used by the computer 144 to compute the position and orientation of transponder 164. General-purpose computer 144 is programmed and equipped with appropriate input circuitry for processing the signals from the receiver.

Preferably, the receiver circuitry includes a clock synchronization circuit, which is used to synchronize the driver circuits and RF power driver. The RF power driver can operate at a frequency that is an integer multiple of the driving frequencies of field generator coils 156. The marker circuitry can then use the RF signal received by the power coil not only as its power source, but also as a frequency reference. Using this reference, the circuitry in the transponder 164 is able to apply phase-sensitive processing to the current signals generated by the sensor coils, to detect the sensor coil currents in phase with the driving fields generated by field generator coils 156. The receiver can apply phase-sensitive processing methods, as are known in the art, in a similar manner, using the input from the clock synchronization circuit. Such phase-sensitive detection methods enable transponder 164 to achieve an enhanced signal/noise ratio, despite the low amplitude of the current signals in the sensor coils.

Although certain frequency ranges are cited above by way of example, those skilled in the art will appreciate that other frequency ranges may be used for the same purposes.

Circuitry in the transponder 164 also stores a unique identifier, and the unique identifier is also transmitted to the tracking sub-system 150, so that the tracking sub-system 150 can determine the identity of the transponder 164 from which positional data is being received. Hence the tracking sub-system can discriminate between different transponders when multiple transponders are present in the working volume of the magnetic fields 158 of the tracking station 154.

The transponder 164 can be hermetically sealed by encapsulation in a sealant or encapsulant. Preferably the sealant provides any, some or all of the following shielding properties: mechanical shock isolation; electromagnetic isolation; biocompatibility shielding. The sealant can also help to bond the electronic components of the marker together. Suitable sealants, or encapsulants, include USP Class 6 epoxies, such as that sold under the trade name Parylene. Other suitable sealants include epoxy resins, silicon rubbers and polyurethane glues. The marker can be encapsulated by dipping the marker in the sealant in a liquid state and then leaving the sealant to set or cure.

The position of the field generator coils 156 can be adjusted in the vertical and horizontal directions (and also in the third transverse direction) so as to change the position of the working volume of the magnetic fields 158 of the tracking station.

Figure 11:
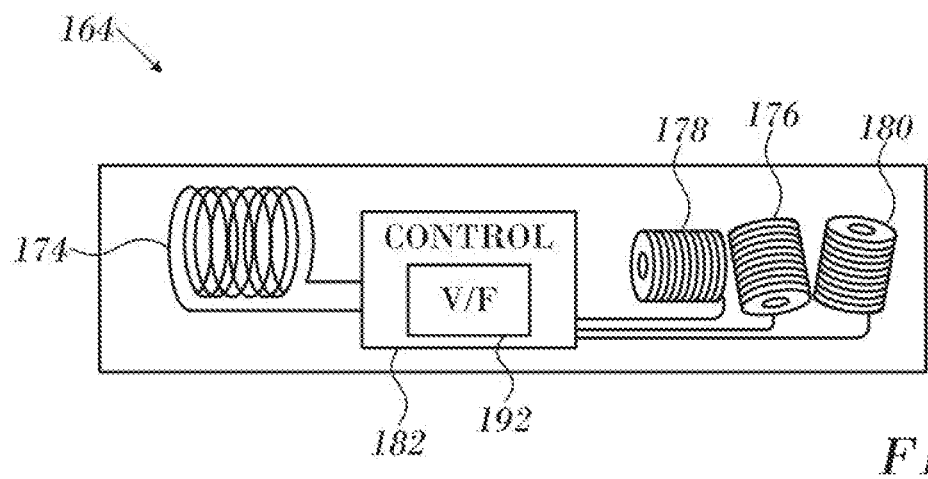
FIG. 11 schematically show details of a transponder in accordance with an alternate embodiment of the invention.

Reference is now made to FIG. 11, which schematically shows details of transponder 164 in accordance with an embodiment of the invention. Transponder 164 comprises a power coil 174 and mutually-orthogonal sensing coils 176, 178, 180, coupled to a control chip 182. Power coil 174 is preferably optimized to receive and transmit high-frequency signals, in the range above 1 MHz. Sensing coils 176, 178, 180, on the other hand, are preferably designed for operation in the range of 1-3 kHz, the frequencies at which field generator coils 156 (FIG. 10) generate their electromagnetic fields. Alternatively, other frequency ranges may be used, as dictated by application requirements. The entire transponder 164 is typically 2-5 mm in length and 2-3 mm in outer diameter.

Figure 12:
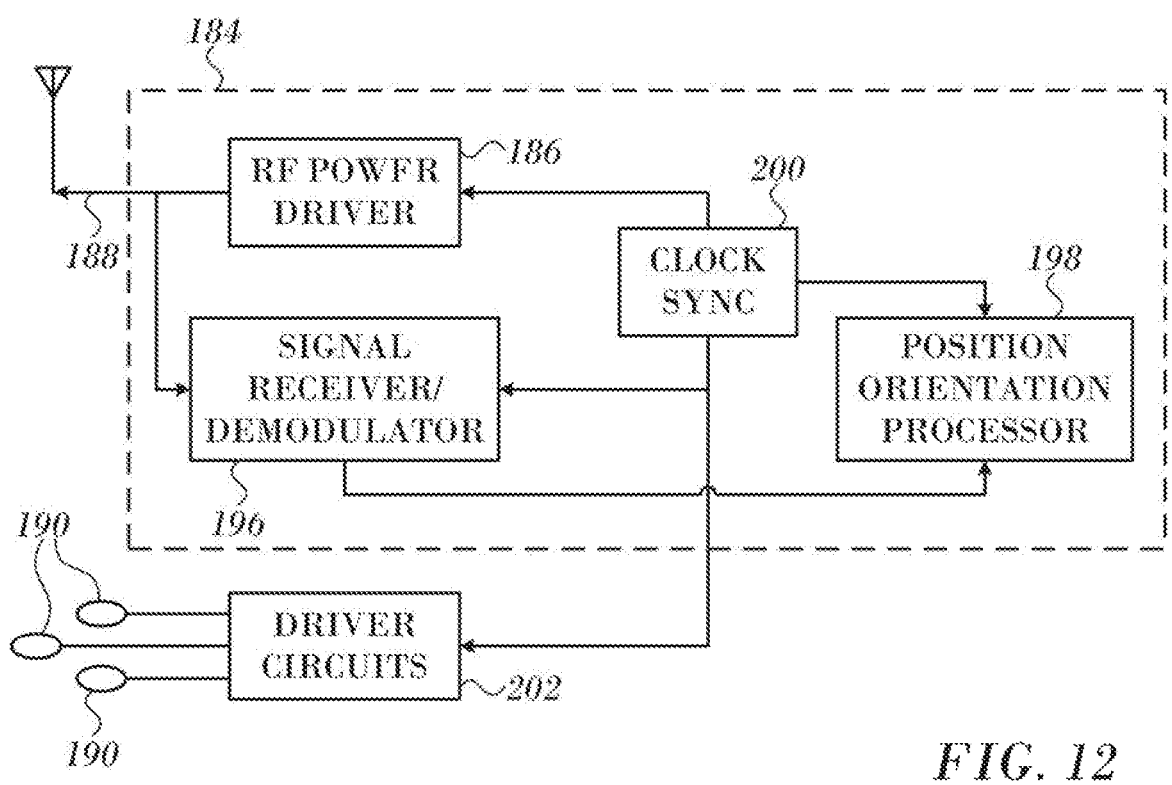
FIG. 12 is a block diagram showing driving and processing circuits in accordance with an embodiment of the invention.

Reference is also made to FIG. 12, which is a block diagram showing driving and processing circuits in a console 184 in accordance with an embodiment of the invention. Console 184 comprises a RF power driver 186, which drives antenna 188 to emit a power signal, preferably in the 2-10 MHz range. The power signal causes a current to flow in power coil 174, which is rectified by chip 182 and used to power its internal circuits. Meanwhile, the electromagnetic fields produced by field generator coils 190 cause a current to flow in sensing coils 176, 178, 180. This current has frequency components at the same frequencies as the driving currents flowing through the field generator coils 190. The current components are proportional to the strengths of the components of the respective magnetic fields produced by the field generator coils 190 in a direction parallel to the axes of the coils 176, 178, 180. Thus, the amplitudes of the currents indicate the position and orientation of the coils 176, 178, 180 relative to the field generator coils 190.

Chip 182 measures the currents flowing in sensing coils 176, 178, 180 at the different field frequencies. It encodes this measurement in a high-frequency signal, which it then transmits back via power coil 174 to antenna 188. Preferably, chip 182 comprises a voltage-to-frequency (V/F) converter 192, which generates a RF signal whose frequency is proportional to the voltage produced by the sensor coil current flowing across a load. Preferably, the RF signal produced by chip 182 has a carrier frequency in the 50-150 MHz range. The RF signal produced in this manner is modulated with three different frequency modulation (FM) components that vary over time at the respective frequencies of the fields generated by coils 176, 178, 180. The magnitude of the modulation is proportional to the current components at the three frequencies. An advantage of using frequency modulation, rather than amplitude modulation, to convey the sensor coil amplitude measurements from transponder 164 to antenna 188 is that the information in the signal (i.e., the frequency) is unaffected by the variable attenuation of the body tissues through which the signal must pass.

Alternatively, chip 182 may comprise a sampling circuit and analog/digital (A/D) converter (not shown in the figures), which digitizes the amplitude of the current flowing in sensing coils 176, 178, 180. In this case, chip 182 generates a digitally-modulated radiofrequency signal, and modulates the signal for transmission by power coil 174. Any suitable method of digital encoding and modulation may be used for this purpose.

The frequency-modulated or digitally-modulated signal transmitted by power coil 174 is picked up by a receiver 196, coupled to antenna 188. The receiver demodulates the signal to generate a suitable input to signal processing circuitry 198 in console 184. Typically, receiver 196 amplifies, filters and digitizes the signals from transponder 164. The digitized signals are received and then used by signal processing circuitry 198 to compute the position and orientation of the transponder 164. Typically, signal processing circuitry 198 comprises a general purpose or embedded computer processor, which is programmed with suitable software for carrying out the functions described hereinbelow. The software may be provided to the processor or processors on tangible non-transitory media, such as CD-ROM or non-volatile memory. Alternatively or additionally, the signal processing circuitry 198 may comprise a digital signal processor, field programmable gate array or hard-wired logic.

In any case, the signal processing circuitry 198 are programmed and equipped with appropriate input circuitry for processing the signals from receiver 196. The information derived by signal processing circuitry 198 is provides other information or guidance to an operator as may be necessary for carrying out a diagnostic or therapeutic procedure.

In an alternative embodiment of the invention, driver 186, receiver 196 and antenna 188 are retrofitted to an existing tracking system, such as the above-mentioned CARTO System. This system may be modified by those skilled in the art to embody the principles of the invention described herein. Console 184 in the existing system is designed to receive and process signals received over wires or wirelessly from one or more sensor coils, using existing signal processing circuitry 198 to determine the position and orientation of the transponder 164. Therefore, in this alternative embodiment, receiver 196 demodulates the signals generated by transponder 164 so as to reconstruct the variable current signals generated by sensing coils 176, 178, 180. The existing processing circuits use this information to determine the position and orientation of the transponder 164 just as if the sensor coil currents had been received by wired connection.

Preferably, console 184 includes a clock synchronization circuit 200, which is used to synchronize driver circuits 202 and RF power driver 186. Most preferably, the power driver 186 operates at a frequency that is an integer multiple of the driving frequencies of the field generator coils 190. Chip 182 can then use the radiofrequency signal received by power coil 174 not only as its power source, but also as a frequency reference. Using this reference, chip 182 is able to apply phase-sensitive processing to the current signals generated by sensing coils 176, 178, 180 to detect the sensor coil current in phase with the driving fields generated by coils 194. Receiver 196 can apply phase-sensitive processing methods, as are known in the art, in a similar manner, using the input from clock synchronization circuit 200. Such phase-sensitive detection methods enable transponder 164 to achieve an enhanced signal/noise ratio, despite the low amplitude of the current signals in sensing coils 176, 178, 180.

The three sensing coils 176, 178, 180 shown in FIG. 11 are sufficient, in conjunction with field generator coils 194, to enable signal processing circuitry 198 to generate three dimensions of position and two dimensions of orientation information of the transponder 164 as well as the third dimension of orientation about its longitudinal axis, as described, for example, in the above-mentioned PCT publication WO 96/05768. The signal processing circuitry 198 can unambiguously determine all six position and orientation coordinates of the transponder 164.

A point of possible ambiguity in determining the orientation coordinates of transponder 164 is that the magnitude of the currents flowing in sensing coils 176, 178, 180 is invariant under reversal of the direction of the axis of the coil. In other words, flipping transponder 164 by 180 degrees through a plane perpendicular to the axis of the sensor coil has no effect on the current amplitude. Under some circumstances, this symmetrical response could cause an error of 180 degrees in determining the coordinates of the transponder.

While the magnitude of the sensor coil current is unaffected by flipping the coil axis, the 180 degree reversal does reverse the phase of the current relative to the phase of the driving electromagnetic fields generated by field generator coils 190. Clock synchronization circuit 200 can be used to detect this phase reversal and thus overcome the ambiguity of orientation under 180 degree rotation. Synchronizing the modulation of the radiofrequency signal returned by chip 182 to receiver 196 with the currents driving field generator coils 190 enables receiver 196 to determine the phase of the currents in sensing coils 176, 178, 180 relative to the driving currents. By checking whether the sensor currents are in phase with the driving currents or 180 degrees out of phase, signal processing circuitry 198 is able to decide in which direction the transponder is pointing.

It will be appreciated by persons skilled in the art that the invention is not limited to what has been particularly shown and described hereinabove. Rather, the scope of the invention includes both combinations and sub-combinations of the various features described hereinabove, as well as variations and modifications thereof that are not in the prior art, which would occur to persons skilled in the art upon reading the foregoing description.

The invention claimed is:

1. An apparatus, comprising:
a shell, conformable to a limb of a patient;
a drill guide assembly moveably mounted on the shell, and having a plurality of radiopaque markers affixed thereon;
a magnetic field generator;
a plurality of magnetic location sensors responsive to magnetic fields produced by the magnetic field generator and linked to a position processor that is operative to compute positional information of the magnetic location sensors; and
a first flange and a second flange attached to the shell; and
rails extending between the first flange and the second flange, wherein the drill guide assembly is mounted on the rails and moveable thereon,
wherein the drill guide assembly comprises parallel struts that are transverse to the rails, wherein the rails pass through transverse bores in the struts, wherein the struts support a plate that is connected with a ball joint having drill guide tunneled therethrough,
wherein the ball joint is adapted to allow free rotation of the drill guide but does not allow translation, wherein the ball joint has a sensor thereon adapted to indicate orientation of the drill guide to an operator.

2. The apparatus according to claim 1, wherein the position processor is operative to place the positional information in registration with a radiographic image.

3. The apparatus according to claim 1, wherein the position processor is disposed on the shell.

4. The apparatus according to claim 3, wherein the position processor further comprises circuitry for driving the magnetic field generator.

5. The apparatus according to claim 1, wherein the shell and the drill guide assembly are radiolucent.

6. The apparatus according to claim 1, wherein there are three magnetic location sensors.

7. The apparatus according to claim 1, wherein there are five magnetic location sensors.

8. The apparatus according to claim 1, wherein the drill guide assembly comprises a ball joint having a bore formed therethrough and dimensioned to admit a drill bit.

9. The apparatus according to claim 8, wherein one of the magnetic location sensors is disposed on the ball joint.

10. The apparatus according to claim 1, wherein the magnetic location sensors communicate location signals wirelessly with the position processor.

11. A method, comprising:
providing a shell, conformable to a limb of a patient, a drill guide assembly moveably mounted on the shell, and having a plurality of radiopaque markers affixed thereon;
generating magnetic fields; and
sensing the magnetic fields using a plurality of magnetic location sensors;
transmitting signals from the magnetic location sensors to a position processor;
and responsively to the signals computing with the position processor positional information of the magnetic location sensors,
wherein the shell comprises:
a first flange and a second flange attached thereto; and
rails extending between the first flange and the second flange, wherein the drill guide assembly is mounted on the rails, the method further comprising translating the drill guide assembly on the rails,
wherein the drill guide assembly comprises parallel struts that are transverse to the rails, wherein the rails pass through transverse bores in the struts, wherein the struts support a plate that is connected with a ball joint having drill guide tunneled therethrough,
wherein the ball joint is adapted to allow free rotation of the drill guide but does not allow translation, wherein the ball joint has a sensor thereon adapted to indicate orientation of the drill guide to an operator.

12. The method according to claim 11, further comprising placing the positional information in registration with a radiographic image using the radiopaque markers.

13. The method according to claim 11, wherein the position processor is disposed on the shell.

14. The method according to claim 13, further comprising generating the magnetic fields with circuitry in the position processor.

15. The method according to claim 11, wherein the shell and the drill guide assembly are radiolucent.

16. The method according to claim 11, wherein the drill guide assembly comprises a ball joint having a bore formed therethrough and dimensioned to admit a drill bit.

17. The method according to claim 16, wherein one of the magnetic location sensors is disposed on the ball joint.

18. The method according to claim 11, further comprising wirelessly communicating location signals from the magnetic location sensors to the position processor.

* * * * *